United States Patent [19]

Garcia et al.

[11] Patent Number: 4,627,445
[45] Date of Patent: Dec. 9, 1986

[54] GLUCOSE MEDICAL MONITORING SYSTEM

[75] Inventors: Fernando S. Garcia; Hartmut Ginnow-Merkert; Paul J. Anderson; David E. Linde; Bertram J. Hudson, all of Eden Prairie, Minn.

[73] Assignee: Garid, Inc., Eden Prairie, Minn.

[21] Appl. No.: 720,906

[22] Filed: Apr. 8, 1985

[51] Int. Cl.$^4$ ............................................. A61B 5/14
[52] U.S. Cl. ................................ 128/770; 128/329 R
[58] Field of Search ............... 128/303 R, 329 R, 760, 128/763, 767, 770, 771, 633, 636, 637; 73/864.87, 61.1 C; 356/39, 40, 41, 42

[56] References Cited

U.S. PATENT DOCUMENTS

| | | | |
|---|---|---|---|
| 2,940,448 | 6/1960 | Furlong | 128/766 |
| 4,003,707 | 1/1977 | Lübbers et al. | 356/39 |
| 4,203,446 | 5/1980 | Höfert et al. | 128/329 R |
| 4,301,412 | 11/1981 | Hill et al. | 128/637 |
| 4,469,110 | 9/1984 | Slama | 128/770 |

*Primary Examiner*—Edward M. Coven
*Attorney, Agent, or Firm*—Hugh D. Jaeger

[57] ABSTRACT

Hand-held shirt-pocket portable medical diagnostic system for checking measurement of blood glucose, urea nitrogen, hemoglobin, blood components or other body qualities. The system includes the engagement of a disposable needle or lance probe package which carries a chemical reagent strip such as blood reacting chemistry. The system includes a pen structure having a visual readout, a microcomputer, and photosensing circuitry which measures the change of color of the blood reacting chemistry of the disposable probe package. The pen also includes a spring arrangement for actuating a needle or lance into the skin for transferring blood from a finger or other area to the chemical reagent strip. A disposable probe structure package includes configurations for transferring of the blood to the reagent strip of the reagent strip to the blood. The pen can also create a vacuum about a time period that the needle is penetrating the skin. The system includes a verification sequence of the electronics, the chemistry of an unused disposable probe package, the presence of blood sample and multiple readings to average results. The system can also be provided with provisions for storing a plurality of readings, communicating with a personal computer, and can act as an alarm and chime to indicate time periods for blood sensing.

8 Claims, 18 Drawing Figures

GLUCOSE MEDICAL MONITORING SYSTEM

BACKGROUND OF THE INVENTION

1. Field of the Invention

The present invention pertains to medical system for sampling and analyzing blood or any components of the blood for specific readings as to qualities of the blood. One specific use of the present invention is for sensing the accumulation of blood glucose for diabetics. The system is a portable, pocket-size, battery operated, diagnostic system for detection and measurement of blood qualities.

2. Description of the Prior Art

Prior art blood glucose devices have operated on the principle of taking blood from an individual by a variety of methods, such as by needle or lance. An individual then had to coat a paper strip carrying chemistry with the blood, and insert the blood-coated strip into a blood glucose meter or visual comparison against a color standard. There are numerous blood glucose meters on the market, but are instruments which consume space and are not pocketable. The instruments usually have to be carried in a large handbag, or an individual's briefcase, or left at home such as in the bathroom or the bedroom.

Further, the prior art medical apparatus for sensing blood glucose required that an individual have separately available a needle or lance for extracting blood from the individual, strips carrying blood chemistry for creating a chemical reaction with respect to the blood glucose and changing color, and a blood glucose meter for reading the change in color indicating the blood glucose level. The level of blood glucose, when measured by glucometer, is read from a strip carrying the blood chemistry through the well-known process of reflectometers for glucose oxidation.

Monitor/reagent strip systems that are now available on the market have multiple sequential steps that the patient must follow at exact time intervals. Each step is subject to error by the patient. As in most monitors, it is the patient's responsibility to periodically calibrate the monitor against known color standards; validate the efficacy of their reagent strips and technique by immersing the strips in a control solution of known glucose content; and, then comparing the color change visually against the color standard or by using a calibrated monitor.

In the prior art, the procedure for obtaining accurate results from the time a drop of blood is placed on a reagent strip pad to the time the pad color change is read in the monitor is as follows. The patient must stick himself/herself with a lancet. A drop of blood must be squeezed to the surface of the skin. The drop of blood must then be carefully placed on the reagent pad, making sure to cover the pad completely and the pad must never be touched by the finger of the patient to prevent contamination. Once the sample has been applied to the surface of the reagent pad, the patient must press a timer on the monitor. At the end of the timing, the patient must wipe, blot or wash the strip off, using a careful technique. And for most strips, the patient must place the reacted reagent strip into the monitor, and press a test button or close a hatch to obtain results. Prior art commercially available comparable reagent strips or monitors require operator intervention in a prescribed sequence at exact time intervals. The prior art is subject to operator error, sequence, timing, and technique errors. The prior art reagent strips are also subject to contamination which will affect accuracy of measurement.

The present invention overcomes the disadvantages of the prior art by providing a hand-held pocketable medical system which includes an attachable disposable probe package carrying a chemical reagent chemistry for extracting blood from an individual, delivering the blood to the blood sensing reagent, or vice versa, in the disposable needle package, and resulting in a read-out of a level such as blood glucose. The system includes a microcomputer which is software controlled by an internal program and, of course, provisions can be provided for external programming of the microcomputer. The computer controls all timing functions thereby eliminating human error.

SUMMARY OF THE INVENTION

One general purpose of the present invention is a portable, shirt-pocket-size, battery-operated diagnostic device/system for use by health professionals and/or lay patients for the detection and measurement of certain selected chemical agents or substances for the purpose of diagnosis and/or treatment of disease. The application is not restricted to use with human beings. It may also be extended to veterinary medicine animals. One first application is for insulin dependent and non-insulin dependent diabetics for the measurement of glucose in serum, plasma, and/or whole blood.

Another purpose of the present invention is to provide a hand-held pocketable medical system including an engaging disposable needle or lance probe carrying the blood sensing reagent for sensing readings of the blood, such as blood glucose level. The medical system is cost effective and simple to operate by an individual. The reading, such as an individual's glucose level, is displayed on an LCD display on the side of a tubular like pen barrel of the medical system which approximates the size of an ordinary ink pen which can be carried in an individual's shirt pocket. The disposable needle probe packages can be carried in a corresponding hollow tubular pencil carrying a plurality of disposable probe packages for use as needed. The tubular structure resembling a pen contains the hand-held pocketable medical system, and the tubular structure resembling a pencil carries the extra supply of disposable needles. The pen-and-pencil design provides for the utmost peace of mind for the individual.

According to one embodiment of the present invention, there is provided a hand-held pocketable medical system including mechanical or electromechanical pen like structure for actuating a needle in a disposable needle or lance probe package, and for enabling a blood sample inside a finger or on the finger surface to be transferred to blood sensing reagent chemistry, or the blood sensing chemistry to be transferred to the blood. The mechanical structure can assume a variety of spring actuated configurations and can further create a vacuum for drawing the blood outside of the finger. The disposable needle probe package frictionally engages onto a socket at the bottome of the tubular hand-held pocketable medical system such as by snapping, threading, or the like, in place, and is easily releasable and disposable after a single use. The hand-held tubular medical system includes photosensing electronics connected to a microcomputer or custom integrated circuit not only for analyzing the properties of the blood sensing chemistry in the disposable probe package, but also for displaying a readout and storing previous readouts. The electronics includes a verification sequence verifying operability of the electronics including sensing of a low battery condition, verifying the condition of an unused disposable needle package, verifying the presence of a blood sample and subsequently providing multiple readings to provide for an averaging of results. The result will not be displayed until the qualification sequence has been successfully sequenced through verification.

One significant aspect and feature of the present invention is a hand-held pocketable medical system referred to as a "Med Pen" or a "Med Pen Mosquito" which is used to extract a blood sample from the body, subject the sample to chemical analysis, and display the results to the individual. A disposable needle package, referred to as a "Med-Point" carries the blood sensing chemistry consisting of a reagent strip, as well as the needle either for delivering blood to the reagent or for causing the reagent to be delivered to the blood. Additional disposable needle packages can be carried in a corresponding structure similar to that of the medical apparatus referred to as a "Med Pencil."

Another significant aspect and feature of the present invention is a pen like structure which is mechanical, and actuates upon a predetermined amount of pressure being exerted on the skin of an individual's finger. Upon this pressure being sensed, the needle will be actuated down through an individual's skin for the subsequent result of enabling a blood sample to be taken from within the finger or blood sample to occur on the surface of the finger. In an alternative, a button can be pushed actuating the probe into the skin.

A further significant aspect and feature of the present invention is a hand-held pocketable medical system referred to as "Med-Pen Mosquito" which will provide blood glucose readings where the disposable needle probe package carries glucose-oxidase or like chemical reagent, whereby once the blood undergoes a colorometric or potentiometric action proportional to the blood glucose concentration, electronics through the reflectance colorimeter provide for subsequent processing of the photosensing of the blood chemistry for displaying of the results on an LCD display.

A further significant aspect and feature of the present invention is a hand-held pocketable medical system which can be utilized by an individual and only requires the engagement of a disposable needle probe package, subsequent actuation of the apparatus causing a subsequent display on a visual readout for the desired measurement.

Having thus described embodiments of the present invention, it is a principal object hereof to provide a pocketable medical system, including disposable needle packages, which carries blood sensing reagent which engage thereto providing a subsequent readout on a visual display of a quality of the blood.

One object of the present invention is to provide a hand-held pocketable medical diagnostic system denoted as a Med-Pen Mosquito, disposable medical probe as needle packages referred to as Med-Points or Med-Probes which engage onto the Med-Pen, and a hollow tubular pencil referred to as a Med-Pencil for carrying extra disposable needle Med-Point packages. The disposable needle packages carry blood sensing chemistry or chemistry for sensing components of the blood for qualities such as glucose level. Other qualities of any substance can also include urea nitrogen, hemoglobin, alcohol, protein or other qualities of the blood.

Another object of the present invention is a Med-Pen which is a reuseable device containing the electronics and software programming, mechanical apparatus, battery(s), sensor(s), and related circuitry that cause the functional operation to be performed. The Med-Point or Med-Probe is a disposable device containing a needle/lance to obtain a blood sample, typically from a person's finger or toe, and a chemical reagent that reacts with the presence of blood as a function of the amount of glucose present in blood. The chemical reagent is sealed inside the Med-Point probe housing or inside a specific housing for the chemical reagent obviating the effects of contamination (from fingers), moisture, and light, thus improving accuracy and precision of measurement by stabilizing the oxidation reduction or chemical reaction of the reagent prior to use. The sensor(s) in the Med-Pen/Point system measure/detect via colorometric and/or potentiometric analysis of the amount of glucose present. This analog data is converted to a digital readout display quantifying glucose in miligrams per deciliter (mg/dl) or MMOL/L.

An additional object of the present invention is a self-contained automatic system. Once the Med-Pen/Point is depressed against the finger (or other area), no further operator intervention may be required depending upon the specific embodiment. All operations and performance of the system are performed automatically and mechanically/electronically in the proper sequence. Accuracy and precision of the measurement is enhanced because errors due to operator interpretation, operator technique, timing of events, and are thereby removed from operator control and influence due to automatic operation. Pressure of the system against a skin surface of a predetermined amount based on spring constants or other predetermined conditions automatically starts the system and sequences the operations dependent upon the specific embodiment.

Still another object of the present invention is a medical system which is software based and software intelligent. The system is self-calibrating through control commands by the software.

DESCRIPTION OF THE PREFERRED EMBODIMENTS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

Figure 1:
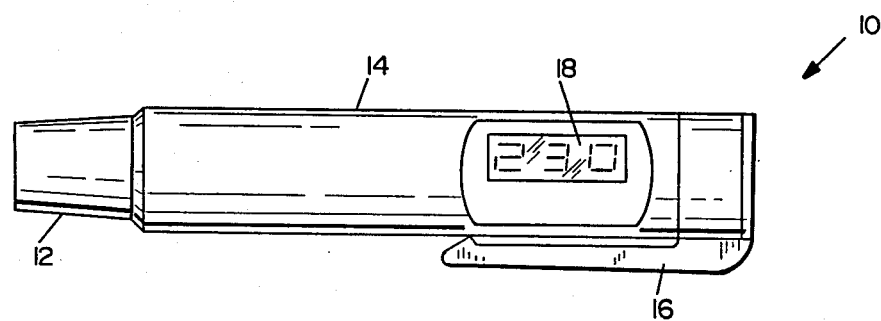
FIG. 1 illustrates a plan view of a hand-held pocketable medical system.

FIG. 1 illustrates a plan view of a hand-held pocketable medical system 10 and a disposable medical probe 12 with a needle or lance or the like carrying blood sensing reagent strip chemistry, all of the present invention. The hand-held pocketable medical system 10 includes a tubular cylindrical pen like member 14 and a clip 16 affixed to the top of the tubular member 14. The disposable medical probe 12 is a narrowing cylinder, and fits into a socket or similar coupling the cylindrical member 25 as later described in detail. A visual electronic readout 18, such as an LCD or the like, including a plurality of digits displays numerical qualities of the blood, as later described in detail.

Figure 2:
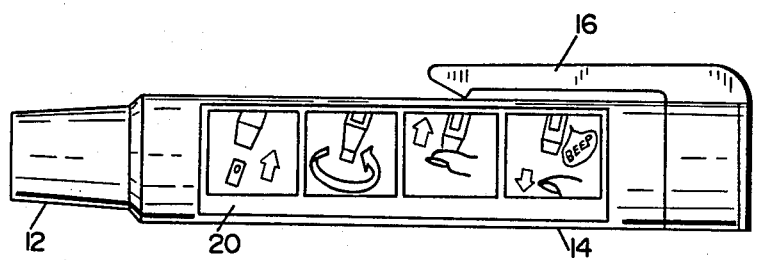
FIG. 2 illustrates an obverse view of FIG. 1.

FIG. 2 illustrates an obverse plan view of FIG. 1 including an instruction panel 20 which can be affixed to the cylindrical tubular member 14 of the system 10.

Figure 3:
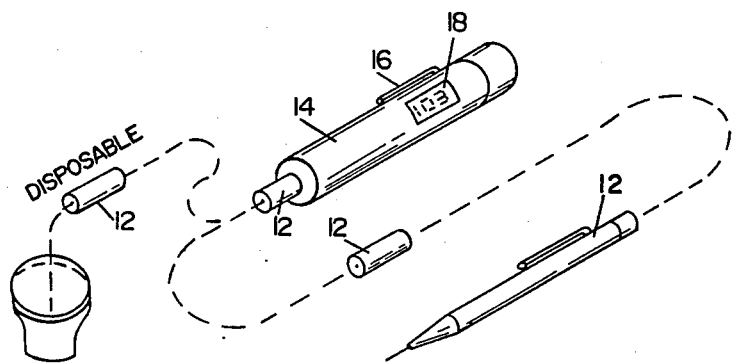
FIG. 3 illustrates a plan view of the system operation.

FIG. 3 illustrates a plan view in perspective of the hand-held pocketable medical system 10, and a disposable medical probe 12 disengaged prior to use and after use. Extra disposable medical probes 12 can be stored in a hollow tubular pencil like cylindrical member 21 which would resemble a pencil like structure.

Figure 4:
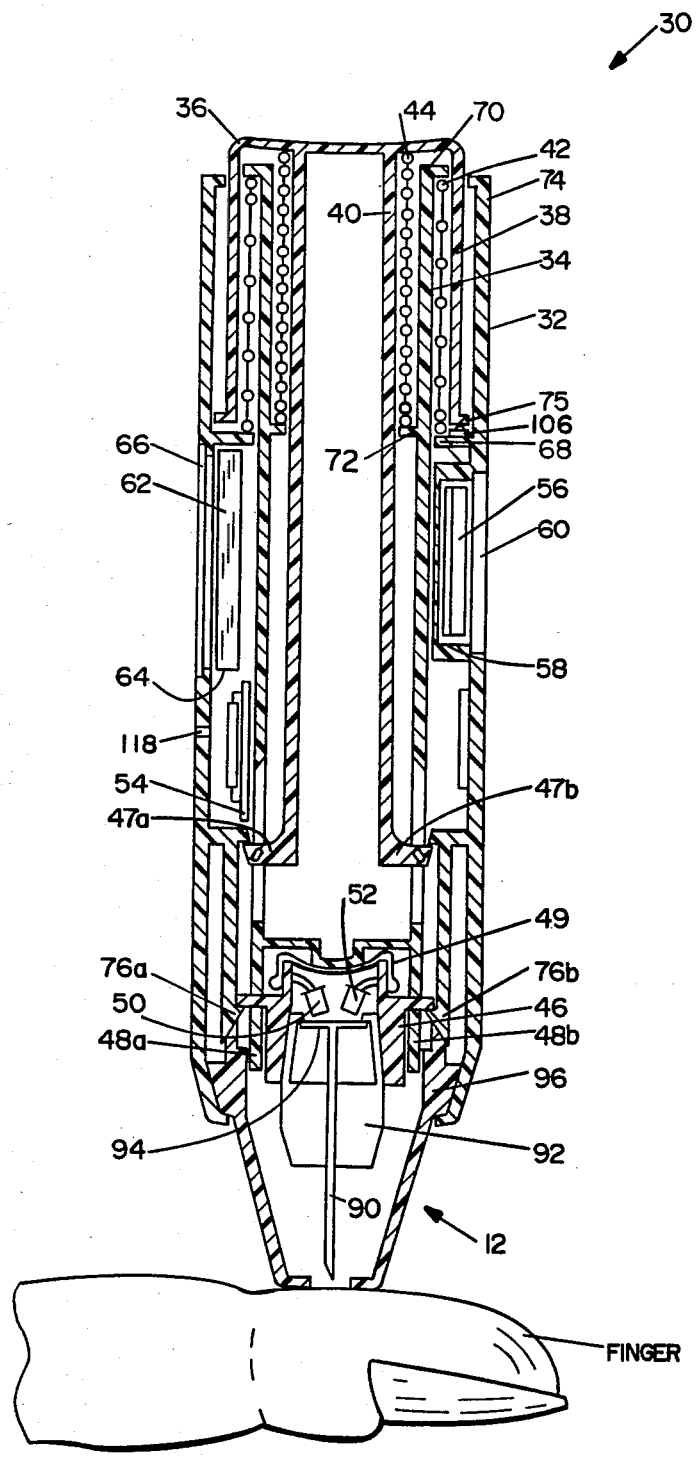
FIG. 4 illustrates a cross-sectional view of a first embodiment.

FIG. 4 illustrates a cross-sectional view of a first embodiment 30 of the medical system 10 prior to finger engagement. The embodiment 30 includes a casing member 32 which is a pen like tubular cylindrical member, and a core portion 34 disposed therein. A button member 36 includes two downwardly extending members 38 and 40 although the button action could be side actuated. An outer spring 42 is disposed between members 38 and 34, and an inner spring 44 is disposed between members 34 and 40. The outer spring 42 is held in position by members 68 and 70. The internal actuating spring 44 is held in position by the lower member 70 and the top of the button 36. Member 74 further limits travel of the button 36 in an upward manner and member 75 limits travel downwardly of button 36. Latch 76a and 76b provide for securing of the diaphragm housing core 46. Latches 47a and 47b are disposed at the lower portion of the downwardly extending member 40. A diaphragm housing core 46 positions in notches 48a and 48b in core part 34. A diaphragm 49 fits over the diaphragm housing core 46. An optical measurement means includes a light source such as LED 50 and a light sensor such as phototransistor 52 mounted in an adjacent and opposed relationship with respect to each other on the walls of the diaphragm housing core 46. The LED 50 and phototransistor 52 connect to an electronics unit 54, as later described in detail. The electronics unit 54 is powered by a battery 56 held in position in battery housing 58 by battery lid 60. A visual display, such as a LCD display 62, positions in a LCD housing 64 and is held therein by a clear viewing lens 66. The disposable probe package 12 includes a needle 90, a probe like supporting structure 92, and a reagent strip 94. The strip 94, while shown in a horizontal configuration, can be in other configurations such as vertical, etc. Release tube 96 which provides means for releasing actuator spring 44, positions in the lower portion of casing 32 and engages the inner surfaces of latches 76a and 76b.

Figure 5:
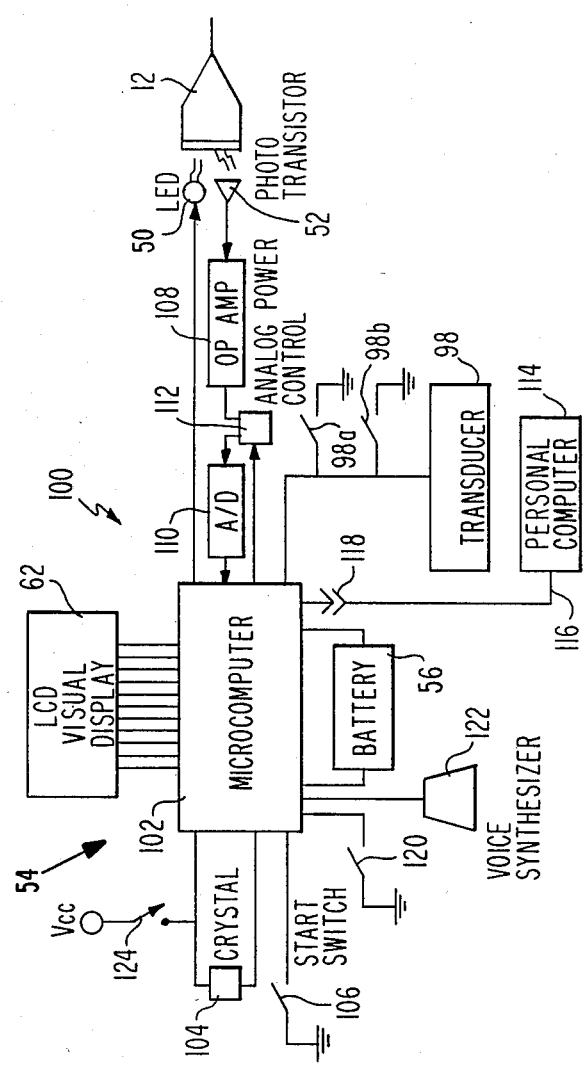
FIG. 5 illustrates an electrical schematic block diagram.

FIG. 5 illustrates an electrical schematic block diagram 100 of the electrical circuitry for the electromechanical structure of FIG. 4. A microcomputer 102 or custom integrated circuit controls operation. A crystal 104 provides the clock signal to the microcomputer 102. A start switch 106 is actuated upon the pressure of the disposable needle 12 against the skin through pressure. An operational amplifier 108 takes an analog signal through to an A/D converter 110. A controller 112 controls power to the op amp 108 and the A/D converter 110. A piezo electric chiming transducer 98 is connected to an internal clock of the microcomputer for chiming at preset times for medical readings. Switches 98a and 98b set the time. A personal computer 114 can connect by a cable 116 to a plug 118 for outputting stored readings. A recall switch 120 recalls each previous reading as the switch is depressed. A voice synthesizer 122 can also state the reading, the time, and the day. The microcomputer stores software to verify the electronics, verify the calibration procedural steps, and controls the measuring of the qualities as predetermined by the software commands. A power wake up switch or photoswitch 124 turns on the electronics when a probe 12 is inserted into the pen 10.

MODE OF OPERATION

The operation of the hand-held portable medical diagnostic system 10 will now be described in detail, particularly with later reference to sensing of glucose for an insulin type of diabetic individual. This is by way of example and for purposes of illustration only and not to be construed as limiting of the structure or mode of operation of the present invention.

Pushing button 36 loads inner actuator spring 44. The push button 36 locks in place by latch 47a and 47b and holds spring 44 in the compressed state as shown in FIG. 4. Diaphragm 49 is thereby compressed by diaphragm tensioner 51 which is a small projection on the central portion of core 34. By pushing the release tube 96 upward with an individual's finger, from which blood sample is to be taken, latches 76a and 76b are opened, and core 34 is forced downwardly by action of the inner actuator spring 44. Downward movement of core 34 drives the diaphragm housing core 46 with the probe 12 and needle 90 downwardly and simultaneously begins to load outer spring 42. Needle 90 punctures the finger. Downward motion of core 34 opens latches 47a and 47b so that push button 36 can return to its neutral position by being forced upward by further expansion of inner spring 44. Outer spring 42, coaxial to inner spring 44, then can push core 34 upwardly which releases the diaphragm 49, and creates a vacuum in diaphragm housing core 46. The vacuum draws blood up from ruptured capillaries in the finger through the needle 90 into the probe 92 whereupon the blood wets the reagent strip 94. Further upward movement of core part 34 pulls the diaphragm housing core 46 upward so that probe 92 and needle 90 retract from the finger. The diaphragm housing core 46 is then locked in place by the latch 76a and 76b, all mechanical action ends, and all elements are in a neutral position. The blood sample on reagent strip 94 is processed by chemical reaction inside reagent strip 94, and color change of strip is read from the opposite side of reagent strip 94 by reflection of light from LED 50 to the phototransistor 52. The signal is processed in electronics of FIG. 5 as later described in detail, and converted into a numeric value subsequently displayed on LCD 62 which reflects the glucose level of the blood sample. The disposable probe 12 is removed from the device by pulling of the probe causing the skirt of casing member 32 to expand, freeing the probe from the socket.

Further operation of the system is now described. A user attaches a Med-Point probe 12 to the Med-Pen system 10 which accomplishes two functions. The first is the Med-Pen and Med-Point are engaged and made ready for use. The second is the sensor(s) can sense predefined color bands/areas located inside Med-Point as the pen and point are mated, thus automatically calibrating through an algorithm in the software. This self calibration ensures accuracy of measurement before each use; eliminates the need for operator intervention and operator induced error; verifies that the chemical reagent inside Med-Point is the correct color, i.e., unreacted; and, causes the Med-Pen to provide a visual and/or audible alarm if the calibration "acceptance criteria" in the software is not satisfied.

The user places Med-Pen/Point on one's finger or other area from which blood sample is to be taken. The user pushes down one end of Med-Pen and holds down until a tactile response indicates Med-Pen/Point may be removed. The tactile response may be in various forms such as mechanical click from detent action or even an audible beep.

Med-Pen/Point performs all operations in the proper sequence and does not require user intervention. A blood sample is transported by vacuum and/or capillary action to the chemical reagent, and/or chemical reagent is transported to the blood sample on surface/within finger or other areas. The vacuum is created by the mechanical action/design of components in the Med-Pen probe. The capillary action is created by the physical dimensional design of the Med-Point probe as later described. An internal clock/timer in the computer is initiated on pressure being exerted in the system. The chemical reagent reacts with blood/glucose. The electronic sensor(s) can detect colorimetrically and/or photoimetrically the amount of glucose present in the blood sample by measuring the change in color of the chemical reagent and/or the conductivity/impedance of the chemical reagent, respectively. The chemical reaction between the reagent and the blood/glucose is time dependent. Multiple measurements are made at specified time intervals as dictated by an internal clock, thus achieving three results. There is improved accuracy due to the resolution of the measurements over shorter time intervals rather than a single measurement at (x) seconds as in the prior art. There is improved accuracy because multiple measurements can be averaged optionally throughout the high/low readings, etc. for linear or non-linear reactions and/or equations. There is faster response time for operator use; i.e., one doesn't have to wait 30–60 seconds for a reading. The system takes early readings and extrapolates. The Med-Pen system electronics converts the analog data to digital format, and displays a quantitative digital readout of glucose in whole blood expressed in mg/dl or MMOL/L.

The accuracy and precision of measurements is further enhanced because the chemical reaction of the chemical reagent is stabilized. The Med-Point housing or self-contained housing for the reagent chemistry can provide a barrier that insulates the chemical reagent from those parameters that accelerate the reaction; i.e., light, moisture, contaminants from fingertips such as salt, fluoride, etc.

The electronics operates on the reflectance colorometer principal where the blood on the reagent strip undergoes a colorometric or potentiometric reaction proportional to the blood glucose concentration. The electronics provides verification of the system, the chemistry of a reagent of an unused strip, the presence of a blood sample, and provides multiple readings to average the results. Several readings can be taken at specific intervals shortly after the blood reacts with the reagent strip. Once two measurements are made at two distinct time periods, the slope of the reaction of the chemistry can be calculated towards determining an actual final glucose value. In the alternative, the software of the microcomputer can control predetermined samplings at predetermined time intervals and average the result to determine the final glucose reading after a predetermined time period, such as 60 seconds. This improves the accuracy of the final reading. The readings can also be stored and either recalled by a switch on the side of the pen, or recalled by connecting the pen through an interconnecting cable to a personal computer for outputting the readings for specific times on specific days to a video display or stored for subsequent display or printout.

DESCRIPTION OF ALTERNATIVE EMBODIMENTS

Figure 6:
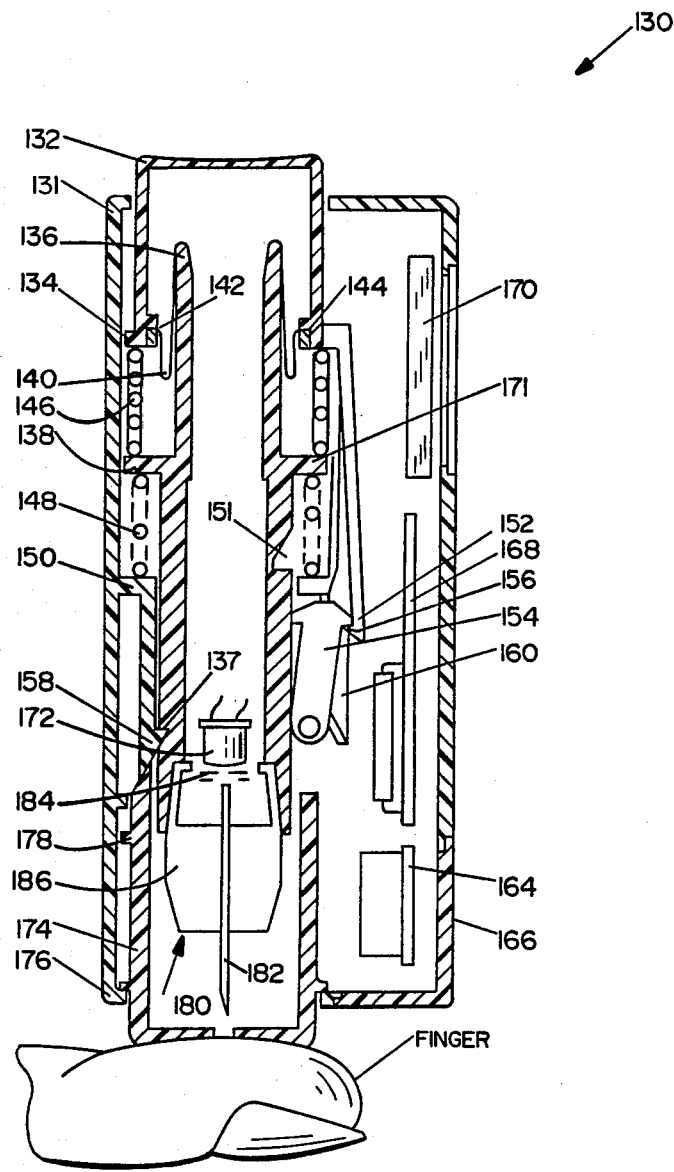
FIG. 6 illustrates a cross-sectional view of a second embodiment.

FIG. 6 illustrates a cross-sectional view of a second embodiment of a medical pen 130. The medical pen 130 includes a housing 131, a button structure 132 including a spring seat 134, a central core 136 including a detent 137, a spring seat 138 and a rolling diaphragm 140 connected between points 142 and 144 of the core 136. Vertically linerally aligned upper actuator spring 146 and lower spring 148 are between spring seats 134 and 138, respectively, and 138 and 150. Upper latch 152 and lower latch 154 engage at point 156. A latch 158 is part of housing 131. A push button extension 160 extends downwardly from the push button 132. The electronics include a battery 164, a battery cover 166, and the microcomputer assembly 168. An LCD display 170 mounts to the internal portion of a battery cover 166 and includes a clear lens 171. A combined optical sensor 172 provides for illumination, as well as detection, of the color of the chemical change. A release tube 174 includes catches 176 and 178. A probe structure 180 includes a needle 182 and a reagent strip 184 and a probe housing 186.

MODE OF OPERATION

Pushing the button 132 downwardly loads spring 146 and locks button 132 in place by action of latch 158 in detent 137. Air inside button 132 is pushed out through core 136, the porous reagent strip 184, probe 186, and the needle 182. The finger from which blood sample is to be taken pushes the release tube 174 upwards, latch 158 is opened so that loaded actuator spring 146 can drive the core 136 down which loads spring 148 and drives needle 182 of probe 186 into finger. Needle 182 ruptures capillaries in finger. When the core 136 has moved all the way down, latch 154 clips into a detent 151 and releases the latch 152 from engagement at point 156. This releases button 132 which is forced back to the neutral position by spring 146. Upward movement of the button 132 creates a vacuum inside button 132 and the core 136 by action of rolling diaphragm 140, that vacuum then reaches probe 186 and needle 182 through porous reagent strip 184, thus sucking blood from capillaries in the finger into the needle 182 through the probe 186 so as to wet the reagent strip 184. Extension 160 of button 132 retracts latch 154 from detent 151 after a mechanical delay and finite time delay defined by distance between latch 158 and extension 160, thus releasing core 136 which is forced upwards by spring 148 which is then locked in place by latch 158. This action retracts probe 186 with needle 182 from finger.

The blood sample on the reagent strip 184 reacts with the reagents in the reagent strip 184 and the resulting color change is read from the opposite side by optical sensor 172, whose signals are converted by electronics into a numerical readout on display which reflects the glucose level of the blood sample. Disposable probe unit 180 is then removed from device.

DESCRIPTION OF ALTERNATIVE EMBODIMENT

Figure 7:
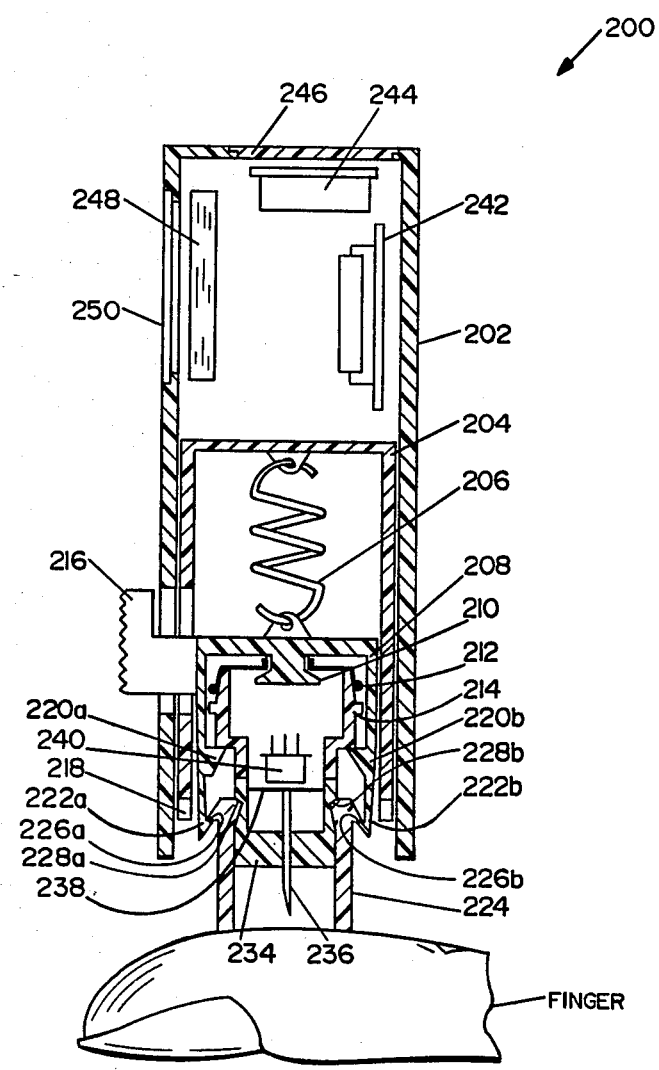
FIG. 7 illustrates a cross-sectional view of a third embodiment.

FIG. 7 illustrates a cross-sectional view of a third embodiment 200. The medical pen 200, an alternative embodiment, includes a casing 202, a spring tensioner 204, a spring 206, a diaphragm tensioner 208, a diaphragm plunger 210, a diaphragm 212, all positioned about a diaphragm housing core 214. This embodiment operates with a single spring 206, which secures between the spring tensioner 204 and the diaphragm tensioner 208. A slide button 216 secures to the diaphragm tensioner 208. The spring tensioner 204 includes an extension 218 extending downwardly therefrom. The diaphragm tensioner 208 includes upper latches 220a and 220b and lower latches 222a and 222b. A release tube 224 secures at points 226a and 226b to the latches 222a and 222b and at junctions 228a and 228b. The probe 234 includes a needle 236 and a reagent strip 238. The electronics include an optical sensor 240, electronic circuitry 242, a battery 244 with a battery cover 246, and an LCD display 248 with a clear lens 250.

MODE OF OPERATION

The probe 234, needle 236, release tube 224, and reagent strip 238 are a single disposable unit which is inserted into the socket in the pen 200. Upward thrust of extension 218 at release tube 224 during insertion pushes spring tensioner 204 upward which loads spring 206. The disposable unit 234 locks into place by action of latch 222a and 222b. Upward thrust of a finger from which blood sample is to be taken opens junction 228a and 228b between release tube 224 and probe 234 because probe 234 stops at the fixed diaphragm housing core 214. Sudden release of the release tube 224 drives the needle 236 into the finger where it ruptures capillaries. At its upper stop, release tube 224 opens latch 220a and 222b on diaphragm tensioner 208 which is forced upward pulling the diaphragm plunger 210 and the diaphragm 212 upward, thus creating a vacuum inside fixed diaphragm housing core 214. The vacuum reaches needle 236 through diaphragm housing core 214 and draws blood from the finger through the needle 236 which wets the reagent strip 238.

The pen 200 has to be manually removed from the finger and reset by means of the slide button 216. The color change of reagent strip 238 is read from the opposite side by the optical sensor 240, and the electronics unit 242 converts the color change into a numerical readout on the display 248.

DESCRIPTION OF ALTERNATIVE EMBODIMENT

Figure 8:
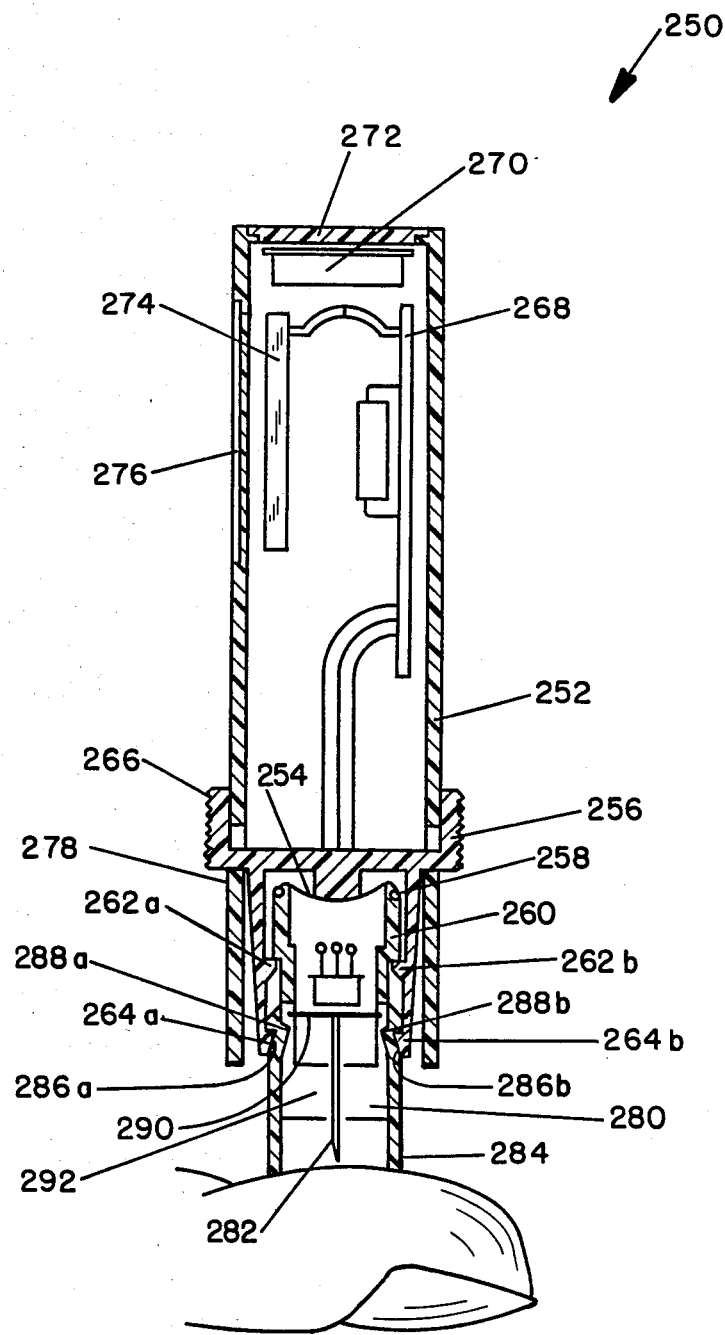
FIG. 8 illustrates a cross-sectional view of a fourth embodiment.

FIG. 8 illustrates a cross-sectional view of a fourth embodiment of a pen 250. The pen 250 includes a casing 252, a diaphragm plunger 254, a diaphragm tensioner 256, and a diaphragm 258. The diaphragm housing core 260 supports the diaphragm 258. Upper latch 262 and lower latches 264a and 264b secure to the diaphragm tensioner 256. A slide button 266 also mounts on the diaphragm tensioner. Internal to the casing 252 are the electronics 268, a battery 270, a screw-on battery cover 272, a display 274, such as an LCD display, and a clear plastic lens 276 inside the casing. Optical sensors 278 connect to the electronics 268. A disposable probe 280 including a needle 282 and a release tube 284 having latch detents 286a and 286b secured to latches 264a and 264b at junctions 288a and 288b. A reagent strip 290 mounts in the probe housing 292.

MODE OF OPERATION

FIG. 8 illustrates the diaphragm tensioner 256 being pushed downward, thus depressing diaphragm 258. Diaphragm tensioner 256 locks into place by the latches 262a and 262b. Probe 280 with the needle 282 and release tube 284 are then inserted and held in place by latches 264a and 264b. Upward thrust of the finger breaks the junction 288 between the probe 280 and the release tube 284 which exposes the needle 282. The needle 282 punctures the finger rupturing the capillaries. At its upper stop, the release tube 284 opens the latches 262a and 262b on the diaphragm tensioner 256 so that by action of the elastic diaphragm 258, the diaphragm tensioner 256 is pushed back. This creates a vacuum in the diaphragm housing core 260 which sucks blood from finger through needle 282 into the probe 280 where the blood wets reagent strip 290. The pen 250 is then manually removed and reset by means of the slide button 266 before the next use. The blood is chemically processed on the reagent strip 290 whose color change is optically read from the opposite side and converted in the electronics unit 268 into a visual readout on display 274. Probe 280 with release tube 284 and needle 282 are held by frictional engagement until removed and disposed of.

DESCRIPTION OF ALTERNATIVE EMBODIMENT

Figure 9:
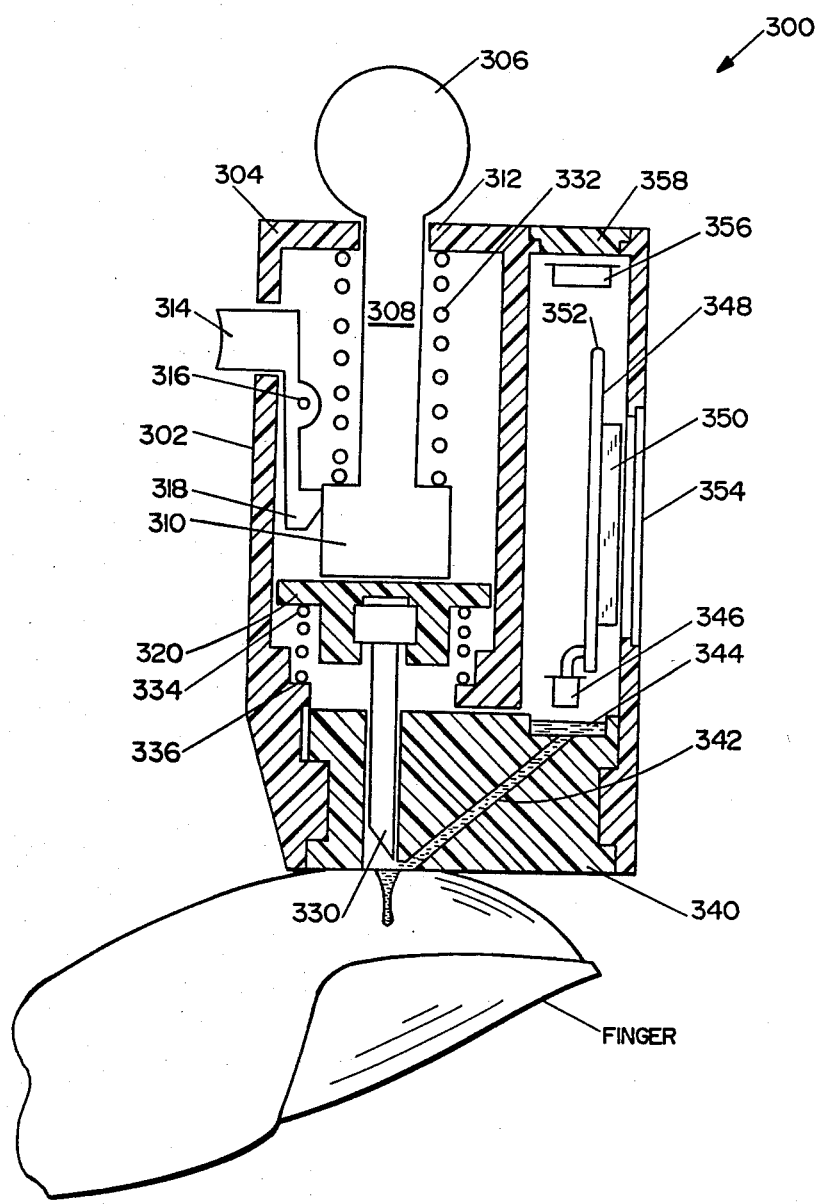
FIG. 9 illustrates a cross-sectional view of a fifth embodiment, a capillary action medical system.

FIG. 9 illustrates a cross-sectional view of a fifth embodiment, a capillary action medical system 300. The capillary action medical system 300 includes a case 302 with a top 304, a knob 306 with a shaft 308, and a plunger 310 fits through a hole 312 in the top 304. A button 314 pivots about a point 316 and includes a latch 318. A lance holder 320 includes a lance 330 therein. An upper spring 332 fits between the top 304 and the top of the plunger 310. A lower spring 334 engages between the bottom of the lance holder 320 and surface 336. A probe 340 includes a capillary duct 342 and a reagent strip 344 therein. Optical sensor 346, microprocessor electronics 348 and an LCD display 350 mount on a board 352. A clear lens 354 fits into the case 302. Likewise, a battery 356 applies power to the electronics unit 348 and includes a battery cover 358.

MODE OF OPERATION

Pulling upwardly on knob 306 loads actuator spring 332, and the plunger 310 then locks in place by latch 318. Disposable unit 340 consisting of the lance 330, probe 340 and reagent strip 344 insert into the system 300. The top end of lance 330 is held by lance holders 320. Pushing the button 314 releases the latch 318. The plunger 310 is forced down, hitting lance holder 320. The lance 330 punctures the finger and ruptures capillary blood vessels. By action of the spring 334, the lance holder 320 returns immediately to its neutral position, retracting the lance 330. Blood starts accumulating in the wound channel, and forms a drop on the skin's surface which is drawn into capillary duct 342 by capillary action. Blood rests on the reagent strip 344 and starts the chemical reaction. Color change is then read from the opposite side by the optical sensors 346 connected to the electronics unit 348. The electronics unit converts signals to a digital readout on display 350.

ALTERNATIVE EMBODIMENTS OF MED POINT

Figure 10:
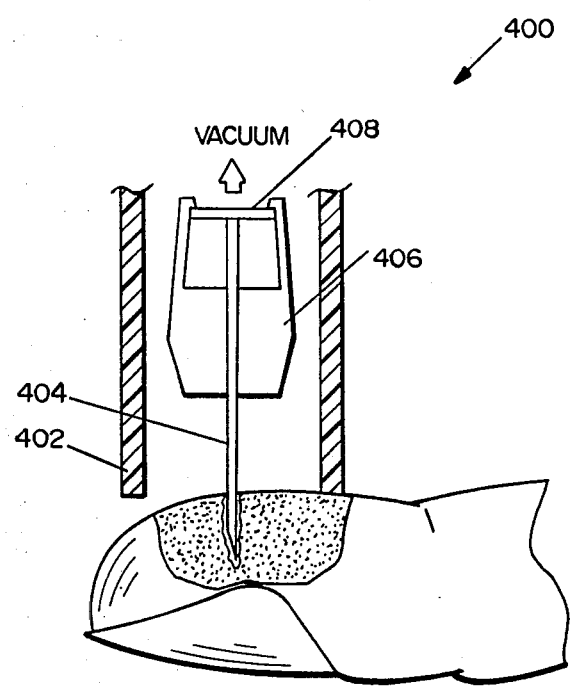
FIG. 10 illustrates a sectional view of a first medical point embodiment.

FIG. 10 illustrates a sectional view of a first embodiment of a medical point 400. A release tube 402 triggers a mechanism in the system 10 which drives a needle 404 into the finger thereby rupturing capillary blood vessels. The blood which accumulates in the wound channel is drawn through the needle 404 into a probe 406 by a vacuum generated in the system, and subsequently onto a reagent strip 408 which can be porous.

Figure 12:
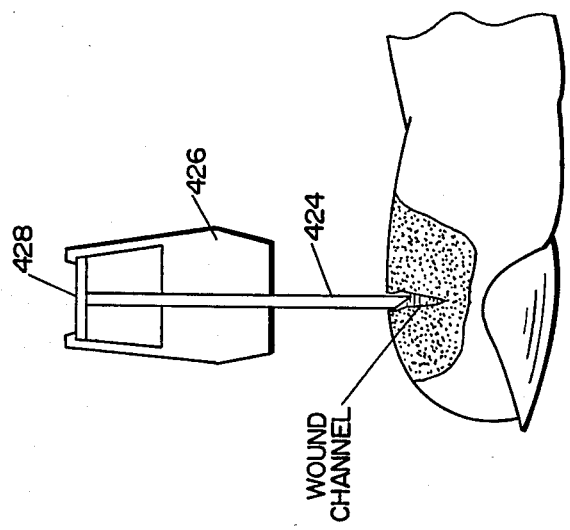
FIGS. 11–12 illustrate sectional views of a second medical point embodiment.
Figure 11:
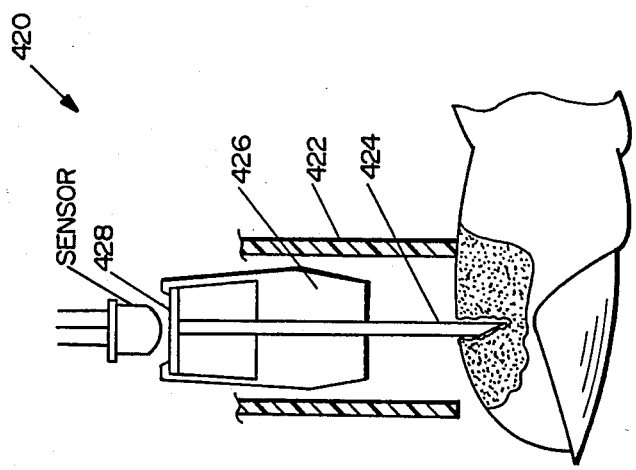

FIGS. 11-12 illustrate a sectional view of embodiments of a medical point 420 having a release tube 422 which is triggered by the system which drives the needle 424 into the finger, thereby rupturing capillary blood vessels. The needle 424 is then retracted halfway in order to allow the blood to accumulate in the wound channel and to avoid being obstructed by the tissue. The blood which accumulates in the wound channel is then drawn through the halfway withdrawn needle into the probe 426 by the vacuum generated in the device and onto the porous reagent strip 428.

Figure 13:
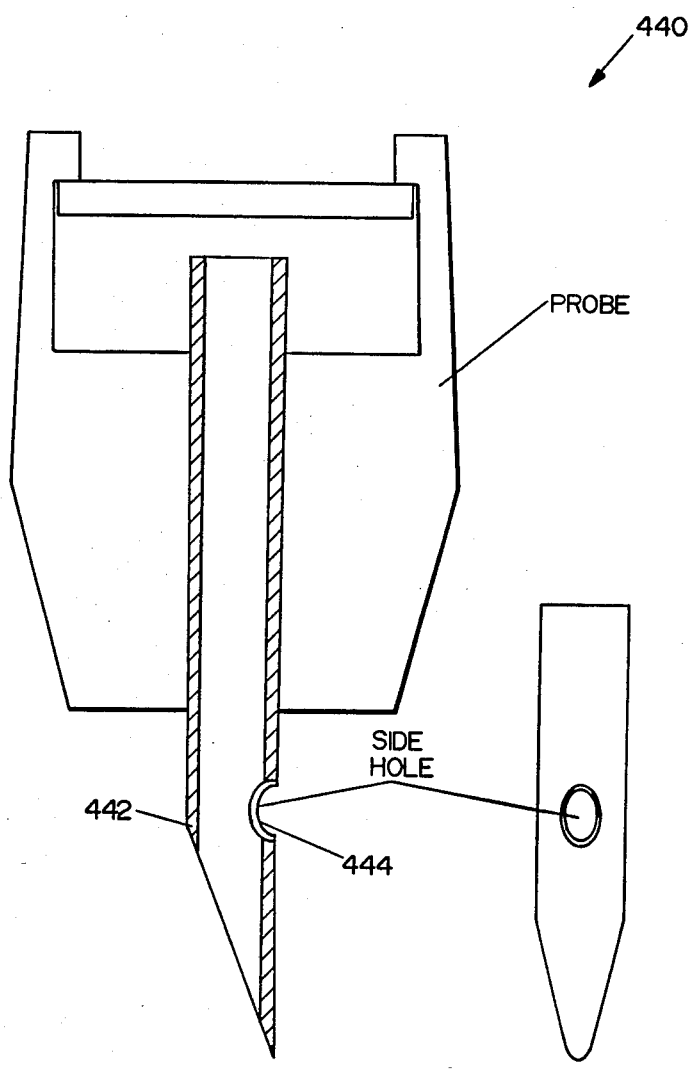
FIG. 13 illustrates a sectional view of a third medical point embodiment.

FIG. 13 illustrates a sectional view of a third medical point embodiment 440 where the needle 442 includes a side hole 444. The needle includes a side hole which provides that the blood can be drawn despite a potentially plugged tip of the needle such as by skin or flesh.

Figure 14:
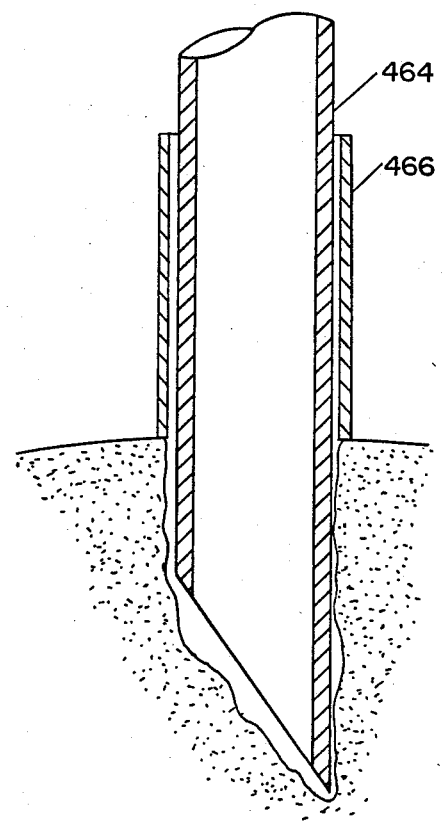
FIGS. 14–15 illustrate a sectional views of a fourth medical point embodiment.
Figure 15:
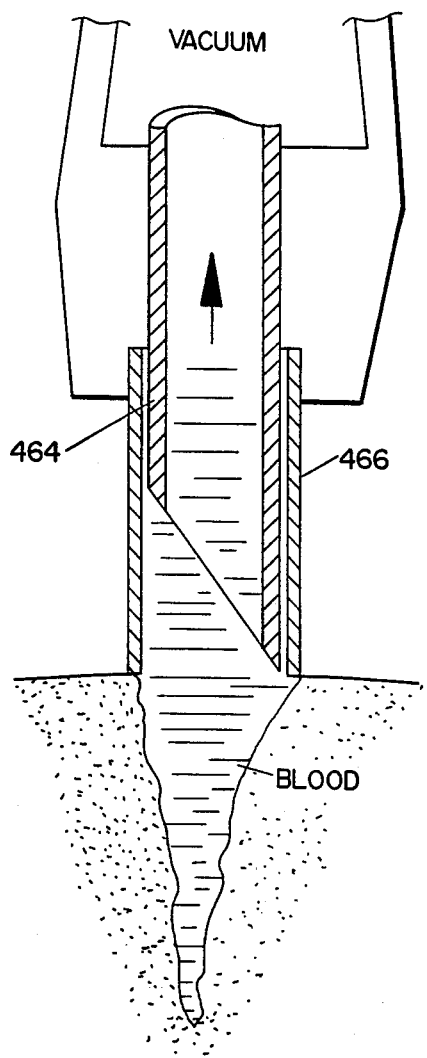

FIGS. 14-15 illustrate sectional views of a fourth medical point embodiment 460 where a needle 464 is enclosed by a side guide tube 466. The side guide tube touches the surface of the finger. After puncturing the finger, the needle 464 is fully retracted in the guide tube 466 and blood is drawn in through the guide tube and the needle as illustrated in FIG. 15. In the alternative, a lance can be utilized in lieu of the needle of FIGS. 14 and 15. The lance can even include a side hole to act as a carrier for carrying the blood in the side hole of the lance.

Figure 16:
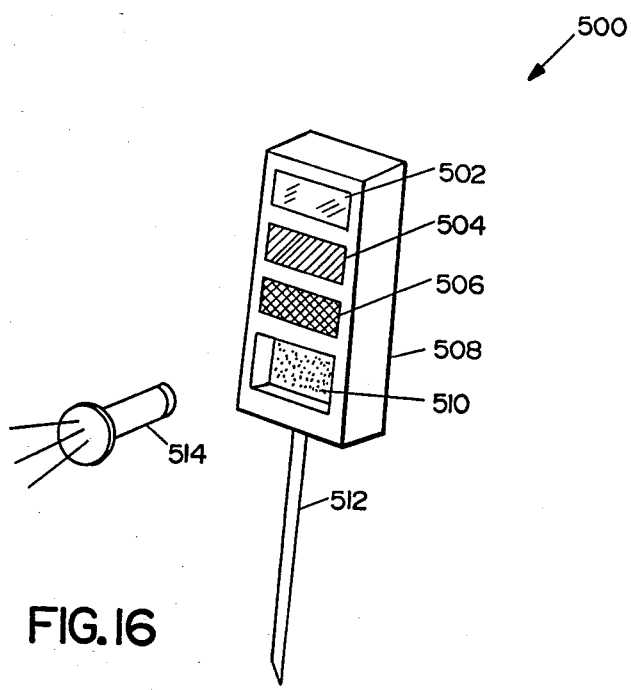
FIG. 16 illustrates a plan view of a system self-calibrating medical point.

FIG. 16 illustrates a plan view of a selfcalibration medical point which includes automatic calibration strips for the optical sensors and microcomputer in the system. The medical point 500 includes color strips 502, 504, and 506 about a probe housing 508. Color strips 502–506 have different shades of grey which reflect three defined levels of glucose in the blood for purposes of calibration. During insertion of the Med-Point, the color strips are read by an optical sensor unit 514. Signals are coupled to the electronics unit for calibration of the Med-Point 500 prior the Med-Point reaching its final position. In the final position, the sensor 514 reads the strip 510, which is impregnated with blood through the needle 512.

Figure 17:
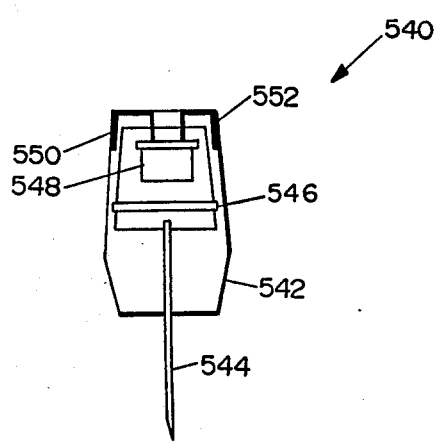
FIG. 17 illustrates a sectional view of a medical probe with self-contained optical sensors; and, FIG. 18 is a flow chart of blood transfer to the reagent strip.

FIG. 17 illustrates a section view of a medical probe 540 including an optical sensing unit 548 with contacts 550 and 552 mounted in a probe housing 542. A needle 544 connects to the reagent strip 546. The optical sensing unit 548 reads the reagent strip and provides electronic information to the Med-Pen device. The metallic contacts 550 and 552 connect the sensing device to the electronics in the Med-Pen. The entire unit is considered disposable based on low cost of volume integrated circuits.

Figure 18:
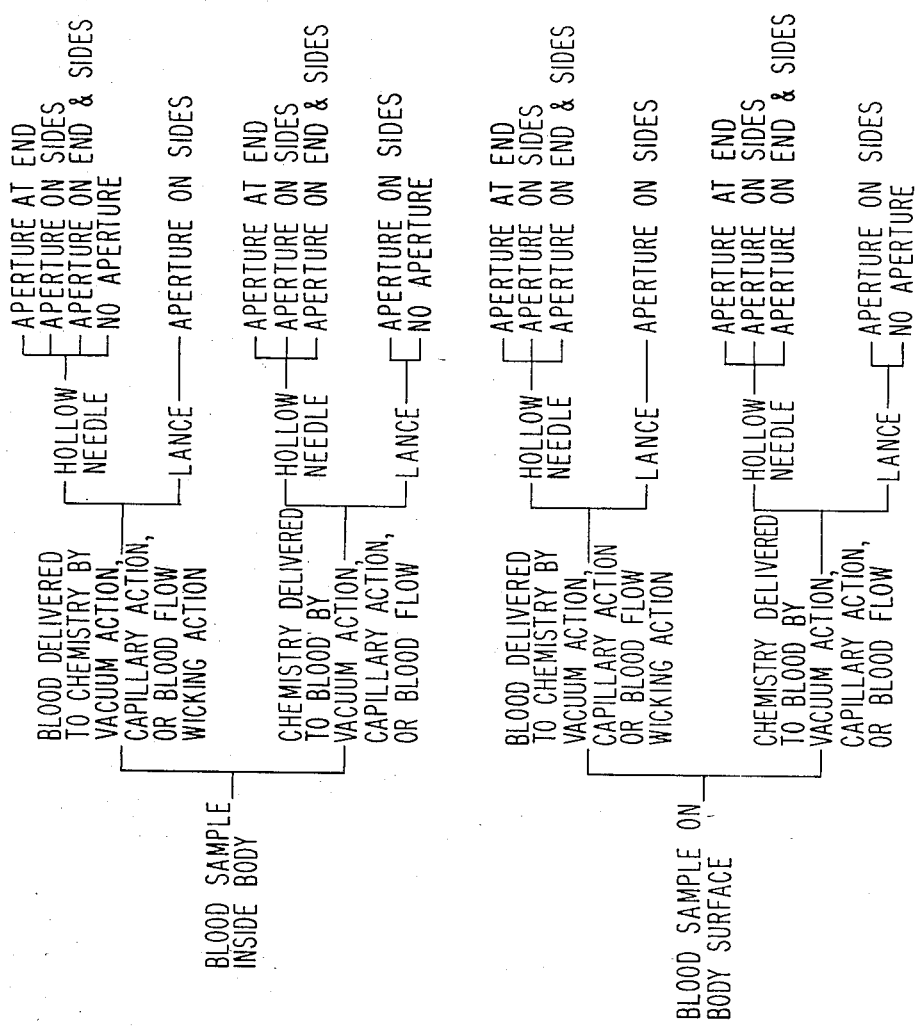

One alternative embodiment of the present invention is that the blood chemistry can be positioned at the site of the blood rather than taking the blood to the blood chemistry reagent strip. Disposable structures can be provided which would snap in place, although a needle or capillary action would not be required in that the reagent strip would touch blood located on one's skin and commence the process. The mode of operation would be that as previously discussed in pushing the system downwardly so that the release tube would apply upper pressure causing a reagent strip to come into contact with the blood. While all of the previous embodiments have illustrated the blood flowing to the chemical sensing reagent strip, the alternative embodiment can take the reagent strip to the blood, such as by having the reagent strip positioned on a lower portion of the disposable probe. The permutations of whether the blood is taken to the reagent strip or the reagent strip is taken to blood, is illustrated in FIG. 18 in a flow chart diagram. The teachings of the present invention can be expanded such as by having the probe include structure for first pricking and bringing blood from below the skin to the surface of the skin, and then having structure for moving the reagent strip to the blood on the surface of the skin for subsequent transfer of the reagent strip to the blood.

We claim:

1. Hand-held pocketable medical diagnostic system for extraction and qualitative analysis of a component of blood in a living body, comprising:

a. housing member including an internal spring actuating means surrounding a contained core means, said spring actuating means including an actuator spring, cocking means for said actuator spring, and means for releasing said actuator spring in response to a predetermined pressure against the skin of a body to move said core means, optical measurement means contained within said housing member, said optical measurement means including a light source and a light sensor in said housing member for measuring light emanating from said source, a blood reagent chemistry between said light source and said light sensor and having an optical characteristic responsive to the component to be measured and in contact with the blood to be measured, said optical measurement means generating an electrical signal proportional to light reflectance of said blood reagent chemistry and therefore also the component of the blood to be measured, display means in said housing member responsive to said electrical signal to provide a visual readout representative of the quantitative analysis, and socket means at one end of said housing member for removably receiving a disposable probe package;

b. disposable probe package shaped to be inserted into said socket means, including said blood reagent chemistry, means for supporting said blood reagent chemistry within said probe package, and a needle supported internal to said probe package below said core means and adjacent to said blood reagent chemistry; and, c. diaphragm means operatively connected to said needle and said blood reagent chemistry for causing vacuum action of said diaphragm means to transport the blood along said needle to said blood reagent chemistry for reaction therewith, thereby resulting in a color change yielding said reflectance of light which is read by said optical measurement means when said spring actuating means through said core means drives said needle through the skin.

2. System according to claim 1 wherein said means for releasing said actuator spring comprises release tube means for unlatching said cocked spring actuating means for driving said needle into said skin.

3. System according to claim 1 wherein
   a. said needle is hollow.

4. System according to claim 3 including spring retracting means in an upper portion of said housing member for actuating said diaphragm means.

5. System according to claim 4 wherein said spring actuating means and said spring retracting means are in coaxial placement within said housing member.

6. System according to claim 1 wherein:
   a. said means for supporting said blood reagent chemistry is transparent; and,
   b. said optical measurement means is positioned to read the optical characteristics of said blood reagent chemistry through said support means from the side of said support means opposite said blood reagent chemistry.

7. System according to claim 1 wherein said needle has at least one side hole.

8. System according to claim 1 wherein said blood reagent chemistry is read from a side opposite that which blood is deposited thereon.

* * * * *